United States Patent [19]

Huskins

[11] 4,072,702
[45] Feb. 7, 1978

[54] TRI-FUNCTIONAL ISOCYANATE CROSSLINKING AGENTS FOR HYDROXY-TERMINATED POLYBUTADIENE BINDERS

[75] Inventor: Chester W. Huskins, Huntsville, Ala.

[73] Assignee: The United States of America as represented by the Secretary of the Army, Washington, D.C.

[21] Appl. No.: 752,636

[22] Filed: Dec. 6, 1976

[51] Int. Cl.$^2$ .............. C07C 119/042; C07C 119/045; C07C 119/048
[52] U.S. Cl. ...................... 260/453 AB; 260/77.5 AT
[58] Field of Search ................................. 260/453 AB

[56] References Cited

U.S. PATENT DOCUMENTS

| | | | |
|---|---|---|---|
| 3,124,605 | 3/1964 | Wagner | 260/453 AB |
| 3,896,154 | 7/1975 | Takahashi et al. | 260/453 AB |
| 3,903,127 | 9/1975 | Wagner et al. | 260/453 AB |
| 4,028,392 | 6/1977 | Ogawa et al. | 260/453 AB |

*Primary Examiner*—Dolph H. Torrence
*Attorney, Agent, or Firm*—Nathan Edelberg; Robert P. Gibson; Jack W. Voigt

[57] ABSTRACT

By use of the reaction for the preparation of biurets from isocyanates (i.e., condensation products of isocyanates and water) a variety of tri-functional isocyanates are made available as the curing agents for rubbery-solid-filled compositions employing hydroxy-terminated polybutadiene (HTPB) binder to obtain beneficial binder chain extension and crosslinking functions.

The tri-functional isocyanates are prepared by the reaction of three moles of a diisocyanate selected from the diisocyanates consisting of dimeryl diisocyanate, isophorone diisocyanate, and trimethylhexamethylene diisocyanate with one mole of water in an appropriate solvent (e.g., p-dioxane). The reaction occurs at solvent reflux temperature. The reaction must be carried out under a blanket of dry nitrogen. The product, a triisocyanate, is obtained ready for use at the end of the reaction when the solvent is stripped from the reaction product. The product achieves improved mechanical properties for a composition containing high solids loadings of either inert ingredients or oxidizer and combustible ingredients depending on intended use for the composition.

3 Claims, No Drawings

TRI-FUNCTIONAL ISOCYANATE CROSSLINKING AGENTS FOR HYDROXY-TERMINATED POLYBUTADIENE BINDERS

DEDICATORY CLAUSE

The invention described herein may be manufactured, used, and licensed by or for the Government for governmental purposes without the payment to me of any royalties thereon.

BACKGROUND OF THE INVENTION

Previously, hydroxy-terminated polybutadiene (HTPB) compositions employing HTPB binders, plasticizers, wetting agents, and high solids loadings were crosslinked with trimethylol propane (TMP) along with isophorone diisocyanate as the isocyanate curing agent which functioned as the crosslinking and chain extension agent. The TMP and other similar compounds have functioned quite well in their field of use; however, the TMP is a solid melting at about 150° F. Therefore the compositions must be mixed or processed at about this or a higher temperature to ensure that the TMP is dissolved.

Desirable would be a crosslinking, curing, and chain extension agent that is not a solid at ambient temperature which would permit composition processing at ambient temperatures.

Therefore, an object of this invention is to provide a variety of multi-functional isocyanates which can serve as curing agents to achieve composition binder chain extension and crosslinking functions.

Another object of this invention is to provide a variety of multi-functional isocyanates which can be used as a mixture in varying the amounts of the di- or tri-functional isocyanates to cure a HTBP polymer composition to obtain a wide range of mechanical properties.

SUMMARY OF THE INVENTION

The tri-functional isocyanates of this invention are prepared by reacting three moles of a diisocyanate with one mole of distilled or deionized water in an appropriate solvent (e.g., p-dioxane). Reaction must be carried out under a blanket of dry nitrogen. The product - a tri-isocyanate is obtained ready for use at the end of the reaction when the solvent is stripped from the reaction product.

The preferred diisocyanates are selected from the diisocyanates consisting of isophorone diisocyanate, trimethyl-hexamethylene diisocyanate, and dimeryl diisocyanate. Other diisocyanates having similar NCO equivalent weight, molecular weights, and other similar physical and chemical properties could be reacted with water to yield tri-functional isocyanates that could serve as crosslinkers in accordance with this invention.

DESCRIPTION OF THE PREFERRED EMBODIMENT

The tri-functional isocyanates of this invention are prepared by combining about 3 moles of a diisocyanate selected from dimeryl diisocyanate, isophorone diisocyanate, and trimethyl-hexamethylene diisocyanate with about 1 mole of distilled or deionized water and reacting under a dry nitrogen blanket and reflux conditions in an excess amount of a dry organic solvent that is non-reactive with the reactants and the reaction products. The solvent should be a solvent for the diisocyanate and the reaction products. P-dioxane is a preferred organic solvent for the reflux reaction media since it boils at about 101.5° C, a moderate temperature, and it is easily stripped from the reaction pot to yield the tri-functional isocyanate. Other organic solvents that have a boiling point within ±20° C of the p-dioxane and that meet the criteria for the reaction solvent can be used in place of p-dioxane.

A typical preparation procedure includes combining together in a reflux vessel in ratio of about 3 moles of the selected diisocyanate with about 1 mole distilled or deionized water in an excess amount of p-dioxane or similar solvent. The reflux reaction is carried out under a dry nitrogen blanket for sufficient time for reaction to be completed (e.g. 1–2 hours) after which the solvent is stripped from the reaction product which is a tri-functional isocyanate (i.e., a biuret type reaction product of the diisocyanate reactant). The reaction product is analyzed by established procedures for the isocyanate value and equivalent weight. The reaction product is ready for immediate use as a crosslinking agent for hydroxy-terminated polybutadiene binder systems. The NCO value and equivalent weight analyses provides the data on the amount to use for the desired NCO content in the binder system to achieve the desired cure, mechanical and physical properties.

The tri-functional isocyanates of this invention are prepared by the reaction represented by the following chemical equation:

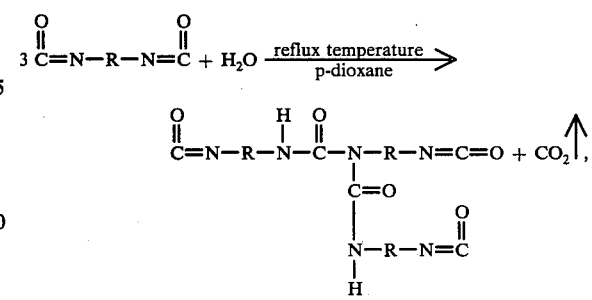

wherein R is derived from a diisocyanate selected from the diisocyanates consisting of isophorone diisocyanate, dimeryl diisocyanate, and trimethylhexamethylene diisocyanate.

Isophorone diisocyanate ($R^o$) has the structural formula:

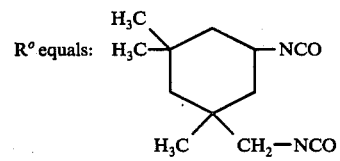

The

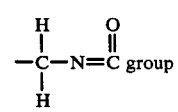

is most reactive; thus, when R is derived from isophorone diisocyanate the triisocyanate derivative of isophorone diisocyanate is illustrated as follows:

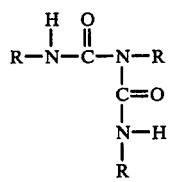

wherein R is R⁰ minus the NCO attached to the CH₂ group of R⁰.

The molecular weight of the triisocyanate derivative of isophorone diisocyanate is 640.9 grams per mole. The isocyanate equivalent per gram is therefore: $3/640.9 = 0.00468$ isocyanate equivalent per gram.

A similar tri-functional isocyanate derivative can be prepared by the same reaction as noted for isophorone diisocyanate when using dimeryl diisocyanate (DDI) structural formula:

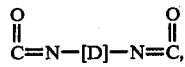

wherein D is a 36 carbon hydrocarbon radical.

The tri-functional isocyanate derivative of dimeryl diisocyanate (TDDI) is prepared by the reaction as follows:

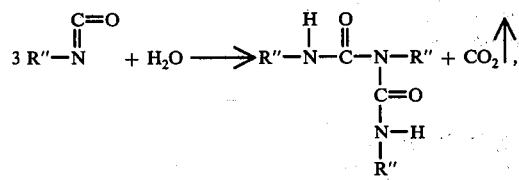

wherein R" is

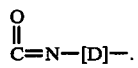

The resulting tri-functional isocyanate derivative (TDDI) has a molecular weight of 1774. The isocyanate equivalent per gram therefore: $3/1774 = 0.00169$ isocyanate equivalent per gram.

Similarly, the derivative of trimethyl-hexamethylene diisocyanate is prepared and the NCO equivalents are calculated for composition compounding use.

The triisocyanate derivative of the isophorone diisocyanate has 2.75 times the equivalents of isocyanate per gram as compared to the similar triisocyanate derivative of dimeryl diisocyanate. Further interpretation means that the formulation of a composition would require 2.75 times as much of the triisocyanate derivative of dimeryl diisocyanate as it would require of the triisocyanate derivative of isophorone diisocyanate.

The review of mechanical properties of polymeric compositions containing the tri-functional isocyanates of this invention indicate that the stress value increases to a maximum value as the NCO/OH ratio of the polymeric system is increased to an optimum value after which additional increases in the NCO/OH ratio actually cause a lower stress value. For the low NCO/OH ratio, the polymeric system does not contain enough OH groups for complete chain extension or crosslinking, thus low stress value. Where there is an excess of NCO groups, there is not enough OH groups to go around; therefore, complete chain extension is not achieved which results in a low stress value polymeric system. Maximum stress at optimum NCO/OH ratio is at the peak of the curve obtained when stress, psi on the ordinate is plotted against NCO/OH on the abscissa.

Polymeric compositions were prepared to evaluate the crosslinking characteristics of the triisocyanate derivative of isophorone diisocyanate. The polymeric compositions are set forth in Table I which also includes mechanical properties and other comparative data for the cured compositions. Composition A is a control composition which includes a curing agent of isophorone diisocyanate. Compositions B and C includes reduced amounts of the curing agent isophorone diisocyanate plus the tri-functional derivative of isophorone diisocyanate of this invention.

The ingredient solids-fillers shown in Table I can include inert solids such as inorganic salts or oxides, asbestos, carbon black, etc. - if a rubbery product substantially non-combustible is desired; however, if a highly combustible rubbery product is desired then oxidizers, metal fuels, and combustible solids would be included along with selected plasticizers of either the energetic type or non-energetic type.

TABLE I

| Ingredient Symbols | Ingredients | Polymeric Compositions* | | |
|---|---|---|---|---|
| | | A (Control) | B (Novel) | C (Novel) |
| HTPB | Hydroxy-terminated polybutadine (binder) | 7.99 | 7.87 | 7.81 |
| BA114 | BA114** (wetting agent) | .30 | .30 | .30 |
| | Plasticizers*** | 6.00 | 6.00 | 6.00 |
| | Solids-fillers | 85.0 | 85.0 | 85.0 |
| IPDI | Isophorone diisocyanate (curing agent) | 0.71 | 0.56 | 0.49 |
| TIPDI | Tri-functional derivative of isophorone diisocyanate (crosslinking triisocyanate) | | 0.27 | 0.40 |
| | Mechanical properties, and other data: | | | |
| | +77° F | | | |
| | Stress, psi | 170.5 | 210 | 234 |
| | Strain, % | 50.9 | 40.5 | 30.8 |
| | Modulus, psi | 525 | 713 | 987 |
| | −40° F | | | |
| | Stress, psi | 529 | 662 | 736 |
| | Strain, % | 39.1 | 30.4 | 27.9 |
| | Modulus, psi | 2348 | 3453 | 4284 |
| | Other data: | | | |
| | NC=O/OH ratio | 1.11 | 1.11 | 1.11 |

TABLE I-continued

| Ingredient Symbols | Ingredients | Polymeric Compositions* | | |
|---|---|---|---|---|
| | | A (Control) | B (Novel) | C (Novel) |
| | End of mix viscosity | 2.0 | 5.0 | 5.0 |

*Ingredients shown in weight percent.
**BA114 (Reaction product of equimolar quantities of 12-hydroxystearic acid and tris[1-(2-amethylaziridinyl)]phosphine oxide (MAPO)) or other processing aids, lecithin etc. are beneficial for processing high solids compositions.
***Plasticizers can be selected from inert light oils, such as isodecyl pelargonate, Circo light oil, polybutenes etc. to adjust viscosity.

To ensure greater compatibility in the hydroxy-terminated polybutadiene binder system wherein used, the curing agent and tri-functional derivative are preferred to be selected from the same species, i.e., if the curing agent is isophorone diisocyanate then the tri-functional derivative of isophorone diisocyanate is preferred for use as the crosslinker.

The following observations are made in evaluating the data of Table I. The NCO/OH ratio was maintained constant at 1.11 which may or may not be the optimum value for these compositions. Increasing the amount of tri-functional diisocyanate while decreasing the amount of isophorone diisocyanate to maintain the NCO/OH ratio constant yielded an increase in the stress and modulus values as compared to the control sample both at +77 and −40° F.

Two additional polymeric compositions were made wherein the NCO/OH ratio was 1.13 and 1.05 which showed lower stress values of 118 and 161 respectively at 77° F and also lower stress values of 492 and 595 respectively at −40° F. The stress values can be lower at a higher or lower NCO/OH ratio than at the optimum NCO/OH ratio. A like stress value can be on the ascending or decending side of a typical stress curve whereas the optimum value of NCO/OH ratio for maximum stress is at peak of curve. The curve drawn from the values of NCO/OH plotted on the abscissa and stress values plotted on the ordinate takes the shape of a hyperbola.

The processing of the polymeric compositions used to illustrate the crosslinking performance of the tri-functional isocyanate derivatives and the curing catalyst can be processed in accordance with established procedures. However, an additional advantage is present in the system for achieving a slower or faster curing since the pot life is proportional to the curing temperature. The action of an optional curing catalyst is accelerated with increased temperature after the propellant is cast. For example, at 120° F a greater curing time is required; however, if a faster curing time is desired the temperature can be increased to 150° F to 170° F without encountering the complexities which may result when using TMP as crosslinker.

Thus, the polymeric compositions in which the tri-functional isocyanate derivatives are effective to adjust the NCO/OH ratio to permit effective crosslinkers include hydroxy-terminated polybutadiene binders (or other polydienes which are similarly cured) in an amount from about 6 to about 12 weight percent; wetting agent in an amount from about 0.2 to about .4 weight percent; solids-fillers up to about 88 weight percent; a diisocyanate curing agent in an amount from about 0.4 weight percent to about 1.0 weight percent selected from the diisocyanates consisting of isophorone diisocyanate, trimethyl-hexamethylene diisocyanate, and dimeryl diisocyanate; and a tri-functional isocyanate derivative in an amount from about 0.2 to about 1.2 weight percent which is a condensation reaction product of three moles of a diisocyanate selected from isophorone diisocyanate, trimethyl-hexamethylene diisocyanate, and dimeryl diisocyanate with one mole of water.

The possible combinations of the tri-functional isocyanate derivatives, the diisocyanate curing agent, and the use of an optional curing accelerator permits a slow cure or a fast cure for the polymeric composition having a wide range of mechanical properties when cured. These properties are a result of the proper adjustment of the NCO/OH ratio and completeness of crosslinking and chain extension of the polymeric binder system under controlled curing conditions.

I claim:

1. A tri-functional isocyanate prepared by the method comprising reacting together in a reflux vessel containing an excess amount of the reacting solvent p-dioxane, three moles of a diisocyanate, and one mole of water selected from distilled water and deionized water, said diisocyanate selected from the group of diisocyanates consisting of isophorone diisocyanate, trimethyl-hexamethylene diisocyanate, and dimeryl diisocyanate, said reacting being carried out under a blanket of dry nitrogen and at reflux conditions for a period of time from about one to about two hours to complete said reacting to form said tri-functional isocyanate in said reacting solvent that is stripped from the reflux vessel to yield said tri-functional isocyanate which is ready for immediate use as a crosslinking agent in a hydroxy-terminated polybutadiene binder system.

2. The tri-functional isocyanate of claim 1 formed from the selected diisocyanate isophorone diisocyanate and having a molecular weight of about 640.9 grams per mole and an isocyanate equivalent of about 0.00468 per gram.

3. The tri-functional isocyanate of claim 1 formed from the selected diisocyanate dimeryl diisocyanate and having a molecular weight of about 1774 and an isocyanate equivalent of about 0.00169 per gram.

* * * * *